United States Patent
Scavone et al.

(12) 
(10) Patent No.: US 6,383,476 B1
(45) Date of Patent: *May 7, 2002

(54) ANHYDROUS ANTIPERSPIRANT AND DEODORANT COMPOSITIONS CONTAINING A SOLID, WATER-SOLUBLE, SKIN ACTIVE AGENT

(75) Inventors: Timothy Alan Scavone, Loveland; Benjamin Scott Schlagheck, Lebanon, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/799,147

(22) Filed: Mar. 5, 2001

(51) Int. Cl.$^7$ .............................. A61K 7/32; A61K 7/34; A61K 7/38
(52) U.S. Cl. .............................. 424/65; 424/66; 424/68; 424/400; 424/401
(58) Field of Search .............................. 424/65, 66, 68, 424/400, 401

(56) References Cited

U.S. PATENT DOCUMENTS

| | | |
|---|---|---|
| 2,780,645 A | 2/1957 | Wehrmeister |
| 2,845,456 A | 7/1958 | Kagan |
| 2,935,528 A | 5/1960 | Kapp et al. |
| 3,275,643 A | 9/1966 | Lubowe |
| 4,970,220 A | 11/1990 | Chaussee |

FOREIGN PATENT DOCUMENTS

| | | |
|---|---|---|
| JP | 12-186014 | 7/2000 |
| WO | WO 00/47169 | 8/2000 |
| WO | WO 00/47170 | 8/2000 |
| WO | WO 00/47171 | 8/2000 |
| WO | WO 00/47182 | 8/2000 |

OTHER PUBLICATIONS

Susan Budavari, Editor et al., "The Merck Index An Encyclopedia of Chemicals, Drugs, and Biologicals", 1989, pp. 255 and 1110, Eleventh Edition, Merck & Co., Inc., Rahway, NJ, USA.

*Primary Examiner*—Shelley A. Dodson
(74) *Attorney, Agent, or Firm*—William J. Winter

(57) ABSTRACT

Disclosed are anhydrous antiperspirant and deodorant compositions that comprise from about 0.1% to about 30% by weight of an antiperspirant or deodorant active; from about 0.1% to about 20% by weight of a water-soluble, skin active solid (e.g., solid, water-soluble vitamins or other nutrients) other than the antiperspirant or deodorant active; from about 0.1% to about 40% by weight of a suspending agent; and from about 10% to about 99% by weight of an anhydrous carrier liquid, wherein the composition is substantially free of nonvolatile organic liquids having a C log P value greater than about 7.0. The anhydrous compositions allow the water-soluble skin active solids to release into the sweat or other moisture on the skin more rapidly or to a greater extent, thus enhancing any skin active effect resulting from such active materials contacting the skin, especially the underarm area of skin.

40 Claims, No Drawings

ANHYDROUS ANTIPERSPIRANT AND DEODORANT COMPOSITIONS CONTAINING A SOLID, WATER-SOLUBLE, SKIN ACTIVE AGENT

The present invention relates to anhydrous antiperspirant and deodorant compositions that contain an antiperspirant or deodorant active, and a solid, water-soluble skin active agent other than the antiperspirant or deodorant active. The compositions provide improved delivery of the water-soluble skin active agent to the skin.

BACKGROUND OF THE INVENTION

Many different antiperspirant and deodorant products are known for use in controlling underarm perspiration and malodor. These products are available in a variety of product forms such as solid sticks, soft solids or creams, roll-on liquids and aerosol or non-aerosol sprays. All of these different products, however, are similar in that they generally have a base formula that contains an antiperspirant active such as an aluminum and or zirconium salt, a suspending or thickening agent, and a suitable liquid carrier.

Antiperspirant and deodorant products typically contain only one skin active ingredient, that ingredient being the antiperspirant and deodorant active. There has been limited disclosure in the literature directed to the addition of other skin active agents to these products to provide the underarm area of the skin with more benefits than mere antiperspirant and deodorant benefits. These disclosures have very recently been directed to the addition of various vitamins to the antiperspirant and deodorant products to provide the underarm area of the skin with benefits associated with such topical vitamin application. Such disclosures have included the topical application of water-soluble vitamins such as ascorbic acid and any of the several Vitamin B materials.

Formulating such other skin active agents into an antiperspirant and deodorant product raises a number of challenges, especially when such products contain water-soluble soluble skin active agents. These water-soluble materials can be formulated as a dissolved active in an aqueous antiperspirant and deodorant formulation, but these aqueous formulations tend to provide less antiperspirant efficacy than similar other anhydrous formulations and leave a wet residue after application that many consumers find undesirable. To avoid these problems commonly associated with aqueous antiperspirant and deodorant formulations, these same products can be formulated as anhydrous products containing the water-soluble skin active agent in the form of dispersed particulate solids. These anhydrous antiperspirant and deodorant products tend to provide better antiperspirant efficacy and application cosmetics.

It has now been found that anhydrous antiperspirant and deodorant products containing solid, water-soluble, skin active materials often provide poor delivery of the water-soluble solid from an anhydrous matrix to the underarm area of the skin. It has also been found that this delivery of such water-soluble solids can be improved by formulating the liquid carrier in the anhydrous product matrix such that the matrix is substantially free of organic liquids having a C Log P value of greater than about 7.0. It is believed that this particular selection of the anhydrous liquid carrier allows for improved dissolution of the water-soluble solid into sweat or other moisture on the skin, which then allows for more effective contact of the water-soluble material with the skin, thus improving the efficacy of the water-soluble material on the underarm area of the skin.

SUMMARY OF THE INVENTION

The present invention is directed to anhydrous antiperspirant and deodorant compositions that comprise from about 0.1% to about 30% by weight of an antiperspirant or deodorant active; from about 0.1% to about 20% by weight of a solid, water-soluble, skin active agent other than the antiperspirant or deodorant active; from about 0.1% to about 40% by weight of a suspending agent; and from about 10% to about 99% by weight of an anhydrous carrier liquid, wherein the composition is substantially free of nonvolatile organic liquids having a C log P value greater than about 7.0.

It has been found that the anhydrous compositions of the present invention allow the solid, water-soluble, skin active agent to release into the sweat or other moisture on the skin more rapidly or to a greater extent, thus enhancing any skin active effect resulting from such active materials contacting the skin. These anhydrous compositions are especially effective when the solid, water-soluble, skin active agent comprises a solid, water-soluble vitamin to provide the skin with skin benefits such as reduced skin wrinkles or other skin imperfections, and or smoother and healthier looking underarm skin.

DETAILED DESCRIPTION OF THE INVENTION

The anhydrous antiperspirant and deodorant compositions of the present invention comprise as essential components an antiperspirant or deodorant active, a water-soluble particulate other than the antiperspirant or deodorant active, a suspending agent, and an anhydrous liquid that is substantially free of certain defined organic nonvolatile liquids. Each of these essential components of the present invention is described in detail hereinafter.

The term "anhydrous" as used herein means that the antiperspirant and deodorant compositions of the present invention, and the essential or optional components thereof, are substantially free of added or free water. From a formulation standpoint, this means that the anhydrous antiperspirant and deodorant compositions of the present invention preferably contain less than about 5%, more preferably less than about 3%, even more preferably less than about 1%, most preferably zero percent, by weight of free or added water, other than the water of hydration typically associated with any particulate solids prior to formulation.

All melting point values referenced herein, unless otherwise specified, are measured and determined according to well known Differential Scanning Calorimetry (DSC) technique. Examples of DSC technique for determining melting point values of various materials are described in U.S. Pat. No. 5,306,514 (Letton et al.), which description is incorporated herein by reference.

The term "ambient conditions" as used herein refers to surrounding conditions under about one (1) atmosphere of pressure, at about 50% relative humidity, and at about 25° C., unless otherwise specified. All values, amounts and measurements described herein are obtained under ambient conditions unless otherwise specified.

The term "volatile" as used herein refers to those materials that have a measurable vapor pressure at 25° C. Such vapor pressures will typically range from about 0.01 mmHg to about 6 mmHg, more typically from about 0.02 mmHg to about 1.5 mmHg, and have an average boiling point at one (1) atmosphere of pressure (atm) of less than about 250° C., more typically less than about 235° C. at one (1) atm. Conversely, the term "non volatile" refers to those materials that are not "volatile" as defined herein.

The term "skin temperature" as used herein refers to the temperature of the axilla area of the skin, which is generally at or slightly below a typical body temperature of about 37° C.

The term "water-soluble" as used herein refers to those materials, including the water-soluble skin active agent as described herein, that can be dissolved in deionized water at 37° C. under otherwise ambient conditions to form an aqueous solution containing at least 0.1% by weight of the dissolved material, preferably at least about 0.5% by weight of the dissolved material.

The anhydrous antiperspirant and deodorant compositions of the present invention can comprise, consist of, or consist essentially of the essential elements and limitations of the invention described herein, as well as any additional or optional ingredients, components, or limitations known or otherwise effective for use in such compositions.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Antiperspirant Active

The anhydrous antiperspirant and deodorant compositions of the present invention comprise an antiperspirant and or deodorant active suitable for application to human skin. The concentration of antiperspirant or deodorant active should be sufficient to provide the desired perspiration wetness or odor control from the anhydrous formulation selected.

The anhydrous antiperspirant embodiments of the present invention preferably comprise antiperspirant active at concentrations ranging from about 0.1% to about 30%, more preferably from about 5% to about 30%, by weight of the composition. These weight percentages are calculated on an anhydrous metal salt basis exclusive of water and any complexing agents such as glycine, glycine salts, or other complexing agents. The antiperspirant active can be solubilized or solid, preferably as dispersed solid particulates. The antiperspirant active as formulated in the composition is preferably in the form of dispersed particulate solids having a preferred average particle size or diameter of less than about 100 μm, preferably from about 1 μm to about 40 μm.

The antiperspirant active for use in the anhydrous antiperspirant embodiments of the present invention include any compound, composition or other material having antiperspirant activity. Preferred antiperspirant actives include astringent metallic salts, especially inorganic and organic salts of aluminum, zirconium and zinc, as well as mixtures thereof. Particularly preferred are aluminum- containing and/or zirconium-containing salts or materials, such as aluminum halides, aluminum chlorohydrate, aluminum hydroxyhalides, zirconyl oxyhalides, zirconyl hydroxyhalides, and mixtures thereof.

Preferred aluminum salts for use in the anhydrous antiperspirant embodiments of the present invention include those which conform to the formula:

$$Al_2(OH)_aCl_b \cdot x\ H_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the anhydrous antiperspirant embodiments of the present invention include those which conform to the formula:

$$ZrO(OH)_{2-a}Cl_a \cdot x\ H_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

Preferred antiperspirant active for use in the compositions of the present invention include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

Antimicrobial Deodorant Active

The antiperspirant and deodorant compositions of the present invention can also be formulated with an antimicrobial deodorant active in addition to or in place of the antiperspirant active. Deodorant active concentrations in such antiperspirant or deodorant compositions may range from about 0.1% to about 30%, preferably from about 0.1% to about 10%, even more preferably from about 0.1% to about 3%, by weight of the composition. These deodorant actives include any known or otherwise safe and effective antimicrobial deodorant active suitable for topical application to human skin, and which is effective in preventing or eliminating malodor associated with perspiration.

Non-limiting examples of preferred antimicrobial deodorant actives for use in the antiperspirant and deodorant compositions of the present invention include cetyl trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4, 4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. Preferred are triclosan, triclocarban, and combinations thereof.

Other deodorant actives suitable for use herein are described in U.S. Pat. No. 6,013,248 (Luebbe et al.), which descriptions are incorporated herein by reference.

Skin Active Agent

The anhydrous antiperspirant and deodorant compositions of the present invention comprise a water-soluble, skin active agent in addition to and other than the antiperspirant and deodorant actives as described herein. The skin active agent can be any water-soluble solid that is known for use in personal care products or which is otherwise suitable for topical application to the skin to provide the desired skin care benefit.

The concentration of the skin active agent will vary substantially depending upon factors such as the particular type of skin active agent selected, the desired effect of that skin active agent on or in the skin, and the compatibility of the skin active agent with the other selected ingredients in the anhydrous antiperspirant composition. Such concentrations will generally, however, range from about 0.01% to about 30%, more typically from about 0.5% to about 20%, by weight of the composition, although the present invention includes higher or lower concentrations of such skin active agents where appropriate.

The solid, water-soluble, skin active agent for use in the anhydrous compositions of the present invention must be in solid particulate form within the composition under ambient conditions, and must also be water-soluble as defined herein.

It has been also found that the anhydrous antiperspirant and deodorant compositions of the present invention have smoother, more consumer-desirable, application cosmetics when the solid skin active agent has an average particle diameter that substantially matches the average particle diameter of any solid antiperspirant or deodorant active in the composition. In this context, the term "substantially matches" means that the average particle diameter of the two solid materials differs by no more than about 40 μm, wherein the average particle diameter of the solid antiperspirant or deodorant active is from about 1 μm to about 40 μm. The average particle diameter of the solid skin care active is preferably from about 1 μm to about 40 μm. The average particle diameter of the solid particles and the agglomerates thereof can of the be measured or otherwise determined using polarized light microscopy methods well known in the various chemical arts.

It has also been found that the solid skin active agent, especially when it contains a water-soluble vitamin such as niacinamide, tends to agglomerate with any solid antiperspirant or deodorant active, especially antiperspirant active, to form undesirably large agglomerated solids within the composition. It has also been found that by milling the intermediate formulation prior to pouring the formulations into packages to cool, that the agglomerates can be reduced or eliminated, thus further improving the application cosmetics of the anhydrous antiperspirant and deodorant compositions. The method by which the milling process is used to reduce or eliminate agglomerate formation is described in greater detail hereinafter.

Non-limiting examples of solid, water-soluble skin active agents for use in the anhydrous compositions of the present invention include crystalline and non-crystalline solids such as water-soluble vitamins, pharmaceuticals, and other skin active materials suitable for topical application to the underarm for the desired skin active benefit or effect. These skin active benefits or effects can include, for example, acute and chronic skin health benefits such as wound healing, anti-wrinkling, smoothening of the skin, depilatory benefits, hair growth regulation or inhibition, anti-oxidation and/or photo-protection, or combinations thereof.

Preferred solid, water-soluble, skin active agents for use in the anhydrous antiperspirant and deodorant compositions of the present invention include natural or synthetic water-soluble vitamins that are at least partially undissolved and in solid particulate form in the anhydrous composition, which includes Vitamin B (thiamine, riboflavin, niacin, pantothenic acid, biotin, cyanocobalamine, pyridoxine, folic acid, inositol,); Vitamin C (ascorbic acid); natural and synthetic derivatives thereof; and combinations thereof. The concentration of these preferred water-soluble vitamins for use in the composition range from above 0.1% to about 20%, more preferably from about 0.1% to about 10%, even more preferably 1% to about 5%, by weight of the composition.

Highly preferred water-soluble vitamins for use in the anhydrous compositions of the present invention include Vitamin B3 compounds and derivatives thereof. In this context, the term "Vitamin B3 compound" refers to those materials that correspond to the formula:

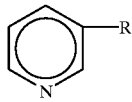

wherein R is—$CONH_2$ (i.e., niacinamide), —COOH (i.e., nicotinic acid) or —$CH_2OH$ (i.e., nicotinyl alcohol); derivatives thereof; and salts of any of the foregoing. Vitamin $B_3$ derivatives include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid for use in the anhydrous antiperspirant and deodorant compositions include nicotinic acid esters of $C_1$–$C_{22}$, preferably $C_1$–$C_{16}$, more preferably $C_1$–$C_6$, alcohols. The nicotinic acid esters are preferably non-rubifacient in that it does not commonly yield a visible flushing response after application from the anhydrous antiperspirant composition, at the selected nicotinic acid ester concentration, to the underarm area of the skin. Non-rubifacient esters of nicotinic acid suitable for use herein include tocopherol nicotinate and inositol hexanicotinate, preferably tocopherol nicotinate.

Other Vitamin $B_3$ derivatives suitable for use in the anhydrous antiperspirant and deodorant compositions include niacinamide derivatives resulting from substitution of one or more of the amide group hydrogens, non limiting examples of which include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C18). Specific examples of such derivatives include nicotinuric acid and nicotinyl hydroxamic acid.

Examples of nicotinyl alcohol esters for use herein include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methylnicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Preferred vitamin $B_3$ compounds for use in the antiperspirant and deodorant compositions of the present invention are niacinamide, tocopherol nicotinate, and combinations thereof, more preferably niacinamide.

Other suitable water-soluble vitamins for use as skin active agents in the anhydrous antiperspirant and deodorant compositions of the present invention include Vitamin B3 salts, including organic or inorganic salts, such as inorganic salts with anionic inorganic species (e.g., chloride, bromide, iodide, carbonate, preferably chloride), and organic carboxylic acid salts (including mono-, di- and tri- C1–C18 carboxylic acid salts, e.g., acetate, salicylate, glycolate, lactate, malate, citrate, preferably monocarboxylic acid salts such as acetate). These and other salts of the vitamin $B_3$ compound can be readily prepared by the skilled artisan, for example, as described by W. Wenner, "The Reaction of L-Ascorbic and D-Isoascorbic Acid with Nicotinic Acid and Its Amide", J. Organic Chemistry, VOL. 14, 22–26 (1949), which description is incorporated herein by reference. Wenner describes the synthesis of the ascorbic acid salt of niacinamide.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed"). More preferably, the vitamin $B_3$ compound is essentially uncomplexed. Therefore, if the composition contains the vitamin $B_3$ compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

The Vitamin $B_3$ compound as a skin active agent in the anhydrous antiperspirant and deodorant compositions is preferably substantially free of salts of a vitamin $B_3$ compound. In this context, the term "substantially free" means that less than 50%, preferably less than 10%, most preferably zero percent, by weight of the Vitamin $B_3$ compound is in salt form.

Other solid, water-soluble, skin active agents suitable for use herein include other water soluble vitamins such as vitamins B1 (e.g., thiamine), B2 (e.g., riboflavin), B5 (e.g., pantothenic acid), B6 (e.g., pyridoxine), B12 (e.g., cyanocobalamine), C (ascorbic acid), and natural or synthetic derivatives thereof. Still other suitable solid, water-soluble skin active materials includes any skin active agent or pharmaceutical that is known for or otherwise suitable in providing benefits to the underarm area of the skin.

SUSPENDING AGENT

The anhydrous antiperspirant and deodorant compositions of the present invention comprise a solid suspending or thickening agent to help provide the compositions with the desired viscosity, rheology, texture and/or product hardness, or to otherwise help suspend any dispersed solids or liquids within the composition.

The term "suspending agent" as used herein, unless otherwise specified, means any material known or otherwise effective in providing suspending, gelling, viscosifying, solidifying and/or thickening properties to the composition or which otherwise provide structure to the final product form. These suspending agents include gelling agents, and polymeric or nonpolymelic or inorganic thickening or viscosifying agents. Such materials will typically be solids under ambient conditions and include organic solids, silicone solids, crystalline or other gellants, inorganic particulates such as clays or silicas, or combinations thereof. It especially important that these materials be solids when at or below body temperature when such materials also have a relatively high C log P value of greater than about 7.0.

The concentration and type of suspending agent selected for use in the antiperspirant and deodorant compositions will vary depending upon the desired product hardness, rheology, formulation (e.g., antiperspirant formulation or deodorant formulation) and/or other related product characteristics. For most suspending agents suitable for use herein, the total suspending agent concentration ranges from about 0.1% to about 40%, more typically from about 0.1% to about 35%, by weight of the composition. Suspending agent concentrations will tend to be lower for liquid embodiments (e.g., aerosols, roll-ons, etc) and higher for semi-solid (e.g., soft solids or creams) or solid stick embodiments.

Non limiting examples of suitable suspending agents include hydrogenated castor oil (e.g., Castorwax MP80, Castor Wax, etc.), fatty alcohols (e.g., stearyl alcohol), solid paraffins, triglycerides and other similar solid suspending esters or other microcrystalline waxes, silicone and modified silicone waxes. Non limiting examples of optional suspending agents suitable for use herein are described in U.S. Pat. No. 5,976,514 (Guskey et al.), U.S. Pat. No. 5,891,424 (Bretzler et al.), which descriptions are incorporated herein by reference.

Other suitable suspending agents include silicone elastomers at concentrations ranging from about 0.1% to about 10%, by weight of the composition. Non-limiting examples of such silicone elastomer materials suitable for use as a suspending agent herein are described in U.S. Pat. No. 5,654,362 (Schulz, Jr. et al.); U.S. Pat. No. 6,060,546 (Powell et al.) and U.S. Pat. No. 5,919,437 (Lee et al.), which descriptions are incorporated herein by reference.

Non-limiting examples of suitable suspending agents for use in deodorant embodiments of the present invention include fatty acid salts such as sodium stearate and other similar materials as described in U.S. Pat. No. 6,013,248 (Luebbe et al.), which description is incorporated herein by reference.

Anhydrous Carrier Liquid

The anhydrous antiperspirant and deodorant compositions of the present invention comprise an anhydrous carrier liquid that is substantially free of all organic nonvolatile liquids having a C log P value greater than 7.0, more preferably greater than 6.5, even more preferably greater than 5.5. The anhydrous carrier liquid can include any volatile or nonvolatile, silicone or non-silicone, carrier liquid that is know for use in personal care compositions or is otherwise suitable for application to the skin.

In this context, the term "substantially free" means that the compositions contain less than 5%, preferably less than 2%, even more preferably less than 1%, most preferably zero percent, by weight of the high C log P organic nonvolatile liquids in the antiperspirant and deodorant composition. In this context, the term "organic liquid" means non-silicone containing materials that are liquid at or below human skin temperature under ambient conditions, or which are otherwise in liquid form at or below human skin temperature once formulated into the finished anhydrous compositions of the present invention.

It has been found that the efficacy of a water-soluble, skin active solid within anhydrous antiperspirant and deodorant compositions is inhibited when the composition is not substantially free of organic nonvolatile liquids having the relatively high C log P values described herein. This is especially significant when the water-soluble, skin active solid, in order to be effective after application, must dissolve in the sweat or other moisture on the skin. It has now been found that the skin active efficacy of such water-soluble skin active solids can be enhanced significantly, or their needed concentration reduced substantially, when the formulation does not contain substantial amounts of these high C log P liquids. It is believed that these high C log P organic liquids form a water-impermeable or water-inhibiting barrier around much or all of the water-soluble skin active solids, thus inhibiting their rate or extent of dissolution and release into the sweat or other moisture on the skin, and thus also inhibiting their efficacy when such efficacy depends upon the rate or extent of dissolution into sweat or other moisture on the skin and the resultant contact with the skin as a solubilized solid.

The high C log P liquids to which the above-described negative limitations apply refer only to nonvolatile organic materials that are liquid at or below human skin temperature (37° C.), and which have a relatively high C log P value as described herein.

Non limiting examples of organic, high C log P, nonvolatile liquids to which this negative limitation applies includes mineral oil, PPG-14 butyl ether, isopropyl myristate, butyl stearate, cetyl octanoate, butyl myristate, C12–15 alkylbenzoate (e.g., Finsolv™), octyldodecanol, isostearyl isostearate, octododecyl benzoate, isostearyl lactate, isostearyl palmitate, and isobutyl stearate. The compositions of the present invention are preferably substantially free of all nonvolatile, organic liquids that are esters, hydrocarbons, hydroxy substituted hydrocarbons, and combinations thereof, which have the high C log P values described greater herein.

It has been found that the antiperspirant and deodorant compositions of the present invention are substantially free of these high C log P, nonvolatile, organic liquids but that high C log P organic materials can be used in the compositions provided that such materials are solids at or below human skin temperature (37° C.) or that such materials are physically or chemically partitioned away from the antiperspirant active in the composition, e.g. encapsulation, emulsification, etc. It has been found that such solids or otherwise partitioned materials do not have the same negative effect on the efficacy of the water-soluble, skin active solid as do the high C log P, nonvolatile, organic liquids described herein.

The use of C log P values is well known in the chemical arts as a calculated value that represents the relative affinity that a material has for partitioning between octanol and water, so that a material that partitions more readily into octanol would tend to be more lipophillic and have a higher C log P value than a material that partitions less readily into octanol. For purposes of defining the antiperspirant and deodorant compositions of the present invention, C log P values are obtained from or calculated by the methods described in Handbook of Physical Properties of Organic Chemicals, Edited by Philip H. Howard and William M. Meylan, CRC Press- Lewis Publishers, 1997, which description is incorporated herein by reference.

C log P values can also be determined by the Pamona Med Chem/Daylight "C LOG P" program, Version 4.42, available from Biobyte Corporation, Claremont, Calif. Other suitable methods for determining C log P values include the fragment approach described by Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990), which description is incorporated herein by reference. Still other suitable methods are described or provided by Daylight Information Systems, Mission Viejo, Calif., Daylight V4.61, Algorithm: V3.05, Database: V16. General information pertaining to C log P values and methodologies are described in Chemical Reviews, 93(4), 1993, 1281–1306, which description is also incorporated herein by reference. As used herein, C log P values include calculated and measured log P values.

The negative limitation directed to nonvolatile, high C log P, organic liquids preferably includes materials that are solid under ambient conditions but that are at least partially melted and in liquid form at or below human skin temperature (37° C.) or which are otherwise in liquid form in the antiperspirant composition as applied topically to the skin. In this context, a material is determined to be liquid at or below human skin temperature by evaluating the material in a finished antiperspirant composition using Differential Scanning Calorimetry (DSC). For example, A Perkin Elmer Model DSC-7 manufactured by Perkin Elmer Corporation, 761 Main Street, Norwalk Conn., can be used to measure a melting profile of the desired material. This is done by preparing a 20 mg sample in a volatile sample pan arrangement of the desired finished product to be tested. The heating curve is generated at 5° C./min and is analyzed by measuring the partial area that melts below 37° C., and those showing at least 10% of the DSC curve below 37° C. are "liquids" for purposes of defining the term "organic liquids" herein.

The anhydrous carrier liquid preferably comprises a volatile silicone liquid, which may include cyclic, linear and/or branched chain silicones having the requisite volatility as defined herein. The concentration of volatile silicone in the antiperspirant and deodorant compositions of the present invention preferably ranges from about 5% to about 80%, preferably from about 20% to about 60%, more preferably from about 30% to about 60%, by weight of the composition.

The volatile silicone is preferably a cyclic silicone having from about 3 to about 7, more preferably from about 5 to about 6, silicon atoms. Most preferred are those that conform to the formula:

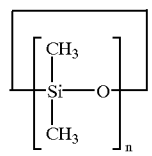

wherein n is from about 3 to about 7, preferably from about 5 to about 6, most preferably 5. These volatile cyclic silicones generally have a viscosity of less than about 10 centistokes. Suitable volatile silicones for use herein include, but are not limited to, Cyclomethicone D5 (commercially available from G. E. Silicones);

Dow Corning 344, and Dow Corning 345 (commercially available from Dow Corning Corp.); and GE 7207, GE 7158 and Silicone Fluids SF-1202 and SF-1173 (available from General Electric Co.).

Non limiting examples of suitable volatile silicones are described in Todd et al., "Volatile Silicone Fluids for Cosmetics", Cosmetics and Toiletries, 91:27–32 (1976), which descriptions are incorporated herein by reference.

The anhydrous liquid carrier may comprise a non-volatile silicone liquid, preferred concentrations of which range from about 1% to about 35%, more preferably from about 5% to about 30%, by weight of the composition. The non volatile silicone carrier is preferably a liquid at or below human skin temperature, or otherwise in liquid form within the anhydrous antiperspirant composition during or shortly after topical application. Preferred are those nonvolatile liquid silicones that conform to either of the formulas:

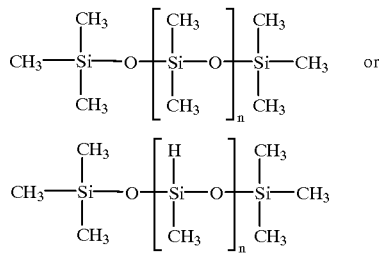

wherein n is sufficiently large to provide a viscosity of up to about 100,000 centistokes, preferably less than about 500 centistoke, more preferably from 10 centistoke to about 200 centistoke, even more preferably from 10 centistoke to about 50 centistoke, as measured under ambient conditions.

Specific non limiting examples of suitable non volatile, linear, silicone carriers include Dow Corning 200, hexamethyldisiloxane, Dow Corning 225, Down Corning 1732, Dow Corning 5732, Dow Corning 5750 (available from Dow Corning Corp.); and SF-96, SF-1066 and SF18 (350) Silicone Fluids (available from G.E. Silicones).

Many other carrier liquids known for use in personal care products can be used in the antiperspirant compositions, alone or in combination with the carrier liquids described in more detail herein, provided that such other carrier liquid is substantially free of the high C log P organic liquids as also described herein.

Optional Ingredients

The anhydrous antiperspirant and deodorant compositions of the present invention may further comprise any optional ingredient that is known for use in antiperspirants and deodorants, or other personal care products, or which is otherwise suitable for topical application to human skin, provided that such optional ingredient is also substantially free of any organic nonvolatile liquid as described herein having a relatively high C log P value.

Non limiting examples of optional ingredients include dyes or colorants, emulsifiers, perfumes, distributing agents, propellants, suspending agent activators, perfumes, preservatives, surfactants, processing aides such as viscosity modifiers, wash-off aids, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

Methods of Manufacture

The anhydrous antiperspirant and deodorant compositions of the present invention may be prepared by any known or otherwise effective technique, suitable for formulating the desired antiperspirant or deodorant product form.

Antiperspirant solid and semi-solid embodiments of present invention can be formulated, for example, by mixing volatile and nonvolatile silicone carrier liquids (or any other desired anhydrous carrier liquid) under ambient conditions, or under conditions sufficient to render the admixture fluid or liquid, and then adding any suspending agents to the mixture and heating the resulting mixture sufficiently to liquefy the added suspending agents, e.g., approximately 85° C. for many wax solids, and form a single phase liquid. Antiperspirant active and other water-soluble solids (e.g., niacinamide, calcium pantothenate, pharmaceutical active, etc.) are then typically added to and dispersed throughout the heated, single-phase liquid before allowing the resulting combination to cool to approximately 78° C., at which point perfumes and similar other materials (if any) are mixed into the combination, which is then cooled to just above the solidification point of the suspending agent (e.g., typically about 60° C.) and then poured into dispensing packages and allowed to solidify under ambient conditions.

Antiperspirant liquid embodiments of the present invention can be formulated, for example, by combining an anhydrous carrier liquid with a suitable suspending agent and activator for the suspending agent and allowing the combination to thicken to the desired viscosity before adding the antiperspirant active and other water-soluble solids with agitation. The resulting mixture is subjected to shear in a suitable homogenizer to achieve the desired concentrate viscosity. For aerosol liquid embodiments, the resulting liquid is then packaged into aerosol containers with an appropriate propellant in a concentrate to propellant ratio suitable for the propellant system selected.

Other suitable methods of making antiperspirant compositions are known and described in the antiperspirant art, and can be used to make the antiperspirant compositions of the present inventions. For solid antiperspirant embodiments, such methods include those described in U.S. Pat. No. 4,822,603 (Farris et al.) and U.S. Pat. No. 4,985,238 (Tanner et al.). For aerosol antiperspirant embodiments, such methods include those described in U.S. Pat. No. 6,136,303 (Ruebusch et al.); U.S. Pat. No. 4,904,463 (Johnson et al.) and U.S. Pat. No. 4,840,786 (Johnson et al.) For soft solid or cream embodiments, such methods are described in U.S. Pat. No. 5,902,571 (Putman et al.) and U.S. Pat. No. 5,902,570 (Bretzler et al.). All such method descriptions in the above-identified patent publications are incorporated herein by reference.

Suitable methods of making deodorant embodiments of the present invention are described, for example, in U.S. Pat. No. 6,013,248 (Luebbe et al.) and U.S. Pat. No. 5,902,572 (Luebbe et al.), which descriptions are incorporated herein by reference.

Preferred Manufacturing Method

The anhydrous antiperspirant and deodorant compositions of the present invention are preferably manufactured by subjecting the composition to a milling step to reduce or eliminate the relatively large solid agglomerates that can form when the solid skin care active is combined with an antiperspirant and deodorant active in solid particulate form.

It has also been found that the solid skin active agent, especially when it contains a water-soluble vitamin such as niacinamide, tends to agglomerate with any solid antiperspirant or deodorant active, especially antiperspirant active, to form undesirably large agglomerated solids within the composition. It has also been found that by milling the intermediate formulation prior to pouring the formulations into packages to cool, that the agglomerates can be reduced or eliminated, thus further improving the application cosmetics of the anhydrous antiperspirant and deodorant compositions.

More specifically, the preferred manufacturing method of the present invention comprises the steps of:

(a) preparing an intermediate composition by mixing together the following components:
 (i) from about 0.1% to about 30% by weight of an antiperspirant or deodorant active;
 (ii) from about 0.01% to about 20% by weight of a solid, water-soluble, skin active agent other than the antiperspirant or deodorant active;
 (iii) from about 0.1% to about 40% by weight of a suspending agent; and
 (iv) from about 10% to about 99% by weight of an anhydrous carrier liquid that is substantially free of nonvolatile organic liquids having a C log P value greater than about 7.0;

(b) heating the intermediate composition to above the melting point of the suspending agent to form a liquid intermediate composition containing solid antiperspirant active and solid, water-soluble, skin active agent, and solid aggregates thereof;

(c) milling the liquid intermediate composition for a period of time sufficient to reduce the average particle diameter of the solid aggregates to less than 50 $\mu$m; and then (d) pouring the milled liquid intermediate into a dispensing package and allowing the packaged composition to cool to ambient temperatures, to form an anhydrous antiperspirant and deodorant composition.

Preferred embodiments of the above-described manufacturing method shall include the preferred formulation embodiments of the compositions described herein, among which is the use of niacinamide as a skin active agent in combination with an aluminum-containing and or zirconium-containing antiperspirant active.

The milling step as referred to herein is any process wherein a shear force is applied that effectively breaks up or reduces any agglomeration of particles and disperses the particles throughout the composition. Non limiting examples of such milling or high shearing mixing processes include colloid milling, high pressure homogenization. The average particle diameter of the solid aggregates after the milling step can be measured or otherwise determined by polarized light microscopy methods well known in the various chemical arts.

Residue Grade

The anhydrous antiperspirant and deodorant solid stick embodiments of the present invention preferably provide low residue performance characterized by a Residue Grade of less than about 50, preferably less than about 40, more preferably less than about 35. In this context, the Residue Grade is an indirect measure of the visible residue that is likely to remain on the skin after topical application of the antiperspirant stick composition.

The Residue Grade as used to characterize preferred embodiments of the present invention is determined by the Naugahyde Method described herein. In accordance with this method, a piece of commercial, black, dull finished, small grained vinyl (Boltaflex vinyl upholstery, Prefixx protective finish, Mfr. GenCorp Polymer Products) cut to a 10 cm×15 cm rectangular strip is placed on a horizontal platform. Each corner of the vinyl strip is then secured with a small binder clip after the material has been slightly stretched to create a smooth surface. An antiperspirant stick under ambient conditions (for at least 24 hours prior to testing) is trimmed flat across the top of the container and placed on a balance which is then tarred to 0.00 grams in order to determine the mass of product to be applied to the vinyl. The stick composition contained within and partially extending out 0.5 cm from a conventional antiperspirant stick package (5.2 cm×2.7 cm topographically oval package) is positioned perpendicular to and above the positioned vinyl by securing the container onto a movable mechanical arm, such that the flat, trimmed surface of the secured product extends out of the package and is facing parallel to the horizontally positioned vinyl. The antiperspirant stick is then slowly moved vertically toward the vinyl sample until the flat, trimmed surface of the product rests upon the far left area of the positioned vinyl. A weight is placed on the product sample so that all of the flat, trimmed surface of the product uniformly contacts the positioned vinyl during testing. The applied weight is selected so as to provide 45.3 grams/cm$^2$ to the trimmed surface of the product sample, e.g., 500 gram weight applied to an oval 5.2 cm×2.7 cm trimmed surface area. The weighted sample is then manually moved repeatedly back and forth across the entire length of the piece of vinyl at a rate of one stroke per second (one stroke equals one left to right movement or one right to left movement), until 0.20 gms.±0.02 gm. of product has been evenly applied over 15.24 cm×5.08 cm area of the black vinyl (0.0026 grams of product per cm$^2$ of the black vinyl surface). The product sample is then removed from the mechanical arm piece and weighed. The vinyl is then unclipped and carefully removed from the platform and dried down for 6 hours.

A calibrated Minolta CR-300 Chroma Meter (available from Minolta Corp., Ramsey, N.J., USA) is then used to measure the L-value (on the L, a, b color scale) of each of the applied vinyl surfaces. For each of the applied vinyl surfaces, twelve random, non-overlapping areas of the applied surface are measured for L-values by the Chroma Meter with its clear plastic view port removed to allow direct placement of the Meter port onto the vinyl so that the meter port is positioned over but without touching the applied vinyl surface. An average L-value is then determined for the twelve measurements which then corresponds to the Residue Grade as described herein.

Method of Use

The anhydrous antiperspirant and deodorant compositions of the present invention may be applied topically to the axilla or other area of the skin in an amount effective to treat or reduce perspiration wetness and or malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied one to two times daily, preferably once daily, to achieve effective antiperspirant and malodor control.

The anhydrous antiperspirant and deodorant compositions of the present invention can be formulated in a variety of product forms and then applied to the axilla or other area of the skin in the manner described herein, such variety product forms including solids (e.g., sticks), semi-solids (e.g., lotions, creams, soft solids), or liquids (e.g. aerosols, non-aerosol sprays, roll-ons, porous dome liquids).

EXAMPLES

The following non-limiting examples described in Tables 1–5 illustrate specific embodiments of the anhydrous antiperspirant and deodorant compositions of the present invention, including methods of manufacture and use. Each of the exemplified compositions is applied topically to the axilla area of the skin, in accordance with the methods of use described herein, and provide improved application or delivery of the water-soluble skin active agent within each composition to the skin. All exemplified amounts are weight percentages based upon the total weight of the antiperspirant stick composition, unless otherwise specified.

Examples 1–3

Antiperspirant Soft Solids/Creams, Wax Sticks, Low Residue Sticks

The Tables 1–3 examples are each prepared as follows. First, the gellants (fully hydrogenated HEAR and C18–C36 acid triglyceride) are dissolved into the silicone liquids, cyclopentasiloxane and dimethicone, by heating the gellants and silicone materials together while stirring on an IKA stir plate to 85° C. The solid antiperspirant active is then added slowly with agitation to the heated mixture, and once added, the resulting mixture is allowed to reheat to 85° C. At this point the solid skin care actives (e.g., niacinamide, calcium pantothenate) are added along with the tocopherol acetate. The mixture is milled at 4 on the speed setting using an IKA brand T 25 Ultra-Turrax disperser using the S 25 N-25F attachment. The product is milled for a period of time sufficient to reduce and break up any agglomerates of solid skin care active or solid antiperspirant active. To measure when sufficient milling has occurred, a small sample of milled product is withdrawn from the hot mixture on a metal spatula and examined under a polarizing microscope. Product is milled until no visible agglomerates greater than 10 microns of skin care active or antiperspirant active are evident. Once milling is completed, then the product is cooled and poured at approximately 60° C. into antiperspirant containers, where it is allowed to cool to ambient temperatures to the desired product form.

TABLE 1

Antiperspirant Soft Solids/Creams

| Ingredients | Example 1.1 | Example 1.2 | Example 1.3 | Example 1.4 |
|---|---|---|---|---|
| Al Zr Trichlorohydrex Glycinate (solid) | 25.25 | 25.25 | 25.25 | 25.25 |
| Dimethicone (10 cs) | 5.00 | 5.00 | 5.00 | 5.00 |
| Fully Hydrogenated High Erucic Acid Rapeseed Oil (HEAR oil) | 5.00 | 5.00 | 5.00 | 5.00 |
| Niacinamide (solid) | 3.50 | 3.50 | 0 | 7.00 |
| C-18-36 Acid Triglyceride Syncrowax HGLC | 1.25 | 1.25 | 1.25 | 1.25 |
| Perfume | 0.75 | 0.75 | 0.75 | 0.75 |
| Calcium Pantothenate (solid) | 0.50 | 0.50 | 3.50 | 1.00 |
| Tocopherol Acetate | 0.50 | 0 | 0 | 0 |
| Cyclopentasiloxane | QS | QS | QS | QS |
| Total | 100.00 | 100.00 | 100.00 | 100.00 |

TABLE 2

Antiperspirant Wax Sticks (Solid)

| Ingredients | Example 2.1 | Example 2.2 | Example 2.3 | Example 2.4 |
|---|---|---|---|---|
| Al Zr Trichlorohydrex Glycinate (solid) | 20.00 | 20.00 | 20.00 | 20.00 |
| Stearyl Alcohol | 11.00 | 11.00 | 11.00 | 11.00 |
| Talc, USP Grade | 6.50 | 7.00 | 7.50 | 3.00 |
| Niacinamide (solid) | 3.50 | 3.50 | 0 | 7.00 |
| Dimethicone (50 cs) | 3.00 | 5.00 | 5.00 | 5.00 |
| Castor Wax | 2.90 | 5.00 | 5.00 | 5.00 |
| Calcium Pantothenate (solid) | 0.50 | 0.50 | 3.50 | 1.00 |
| Tocopherol Acetate | 0.50 | 0 | 0 | 0 |
| Fumed Silica | 0.18 | 0.18 | 0.18 | 0.18 |
| Dipropylene Glycol | 0.18 | 0.18 | 0.18 | 0.18 |
| Microthene | 0.18 | 0.18 | 0.18 | 0.18 |
| Behenyl Alcohol | 0.08 | 0.08 | 0.08 | 0.08 |
| Perfume | 0.75 | 0.75 | 0.75 | 0.75 |
| Cyclopentasiloxane | QS | QS | QS | QS |
| Total | 100.00 | 100.00 | 100.00 | 100.00 |

TABLE 3

Antiperspirant Low Residue Sticks (Solid)

| Ingredients | Example 3.1 | Example 3.2 | Example 3.3 | Example 3.4 |
|---|---|---|---|---|
| Al Zr Trichlorohydrex Glycinate (solid) | 25.25 | 20.00 | 20.00 | 20.00 |
| Dimethicone (50 cs) | 5.00 | 5.00 | 5.00 | 5.00 |
| Fully Hydrogenated High Erucic Acid Rapeseed oil (HEAR oil) | 15.00 | 15.00 | 15.00 | 15.00 |
| Isopar M | 10.00 | 10.00 | 10.00 | 10.00 |
| Niacinamide (solid) | 3.50 | 3.50 | 0 | 7.00 |
| C-18-36 Acid Triglyceride Syncrowax HGLC | 3.75 | 3.75 | 3.75 | 3.75 |
| Perfume | 0.75 | 0.75 | 0.75 | 0.75 |
| Calcium Pantothenate (solid) | 0.50 | 0.50 | 3.50 | 1.00 |
| Tocopherol Acetate | 0.50 | 0 | 0 | 0 |
| Cyclopentasiloxane | QS | QS | QS | QS |
| Total | 100 | 100 | 100 | 100 |

Example 4

Antiperspirant Aerosols

The Table 4 examples of aerosol embodiments can be prepared by methods well know for making aerosol antiperspirant products, such as those methods described in U.S. Pat. No. 6,136,303 (Ruebusch et al.); U.S. Pat. No. 4,904,463 (Johnson et al.) and U.S. Pat. No. 4,840,786 (Johnson et al.). The Table 4 examples can be prepared by combining the water-soluble solids (e.g., niacinamide, calcium pantothenate, etc.) with the solid antiperspirant active in an aerosol container. All other materials are mixed together to form a homogeneous premix liquid before adding the newly formed premix to the aerosol container. The propellant is then added, under pressure, and the container sealed.

TABLE 4

Antiperspirant Aerosols

| Ingredients | Example 4.1 | Example 4.2 | Example 4.3 | Example 4.4 |
|---|---|---|---|---|
| 5/6 Aluminum chlorohydrate solid (Macrospherical –95) Reheis Chemical Company | 10.50 | 10.50 | 11.00 | 10.50 |
| SE76 Silicone Gum[1] | 5.00 | 5.00 | 5.00 | 5.00 |
| SWS 801[2] | 15.00 | 15.00 | 15.00 | 15.00 |
| Cyclomethicone[3] | 3.40 | 3.40 | 3.40 | 3.40 |
| Niacinamide (solid) | 1.00 | 1.00 | 0 | 0.50 |
| Calcium Pantothenate (solid) | 0.50 | 0.50 | 1.00 | 0.50 |
| Vitamin C (solid) | 0 | 0 | 0 | 0.50 |
| Tocopherol Acetate | 0.50 | 0 | 0 | 0.50 |
| Propellant A-46[4] | QS | QS | QS | QS |
| Total | 100.00 | 100.00 | 100.00 | 100.00 |

[1]Silicone gum pre-mix (15% silicone - 15 × 10$^6$ centipoise and 85% cylomethicone); General Electric Company
[2]Diamino-functional silicone, m.w. 76,000; SWS Silicone, inc.
[3]Total cyclomethicone, including that contained in the silicone premix described in note 2.
[4]Mixture of 87% Isobutane and 13% propane (by weight of total propellant)

Example 5

Antiterspirant Liquids

The Table 5 examples are each prepared by combining and mixing together the various components under ambient conditions. Each of the resulting mixtures is then milled on a IKA brand T 25 Ultra-Turrax dispersor (4 speed setting) using the S 25 N-25F attachment. The mixture is subjected to the milling process long enough to reduce and break up any solid skin care active or antiperspirant active agglomerates. The mixture is sufficiently milled when a small sample as examined under a polarizing microscope shows no visible agglomerates greater than 10 microns. Once milling is complete, the liquid antiperspirant product is poured into roll-on antiperspirant containers, or other suitable liquid antiperspirant dispenser.

TABLE 5

Antiperspirant Liquids

| Ingredients | Example 5.1 | Example 5.2 | Example 5.3 | Example 5.4 |
|---|---|---|---|---|
| Al Zr Trichlorohydrex Glycinate (solid) | 21.25 | 21.25 | 21.75 | 20.00 |
| Dimethicone (10 cs) | 10.00 | 10.00 | 10.00 | 10.00 |
| Microthene | 7.00 | 7.00 | 7.00 | 7.00 |
| Bentone 38 | 1.00 | 1.00 | 1.00 | 1.00 |
| Cab-O-Sil | 0.70 | 0.70 | 0.70 | 0.70 |
| Propylene Carbonate | 0.30 | 0.30 | 0.30 | 0.30 |
| Perfume | 0.50 | 0.50 | 0.50 | 0.50 |
| Niacinamide (solid) | 3.50 | 3.50 | 0 | 2.0 |
| Calcium Pantothenate (solid) | 0.50 | 0.50 | 3.50 | 1.0 |
| Vitamin C (solid) | 0 | 0 | 0 | 2.0 |
| Tocopherol Acetate | 0.50 | 0 | 0 | 0 |
| Cyclopentasiloxane | QS | QS | QS | QS |
| Total | 100.00 | 100.00 | 100.00 | 100.00 |

Example 6

Deodorants

The Table 6 examples are each prepared by combining and mixing together the deodorant and skin active solid (e.g., calcium pantothenate, niacinamide, etc.) in an aerosol container. The silicone gum, amino-functionalized silicone, cyclomethicone and fragrance are premixed and added to the can. The propellant is then added, under pressure, and the can sealed. These formulations can be prepared by methods well known in the antiperspirant art, a non-limiting example of which is described in U.S. Pat. No. 4,806,338 (Luebbe et al.), which description is incorporated herein by reference.

TABLE 6

Deodorants

| Ingredients | Example 6.1 | Example 6.2 | Example 6.3 | Example 6.4 |
|---|---|---|---|---|
| Triclosan | 0.3 | 0.3% | 0.3% | 0 |
| Sensiva SC-50[1] | 0 | 0 | 0.6% | 0.6% |
| SE76 Silicone Gum[2] | 5.00 | 5.00 | 5.00 | 5.00 |
| SWS 801[3] | 15.00 | 15.00 | 15.00 | 15.00 |
| Cyclomethicone[4] | 3.40 | 3.40 | 3.40 | 3.40 |
| Niacinamide (solid) | 1.00 | 1.00 | 0 | 0.50 |
| Calcium Pantothenate (solid) | 0.50 | 0.50 | 1.00 | 0.50 |
| Vitamin C (solid) | 0 | 0 | 0 | 0.50 |
| Tocopherol Acetate | 0.50 | 0 | 0 | 0.50 |
| Perfume | 3.0 | 2.0 | 2.0 | 2.0 |
| Propellant A-46[5] | QS | QS | QS | QS |
| Total | 100.00 | 100.00 | 100.00 | 100.00 |

[1]A synthetic representative of the 1-alkyl glycerin ethers with a high degree of purity; mfr. S. A. Schulke & Mayr, Belgium N.V.
[2]Silicone gum pre-mix (15% silicone - 15 × 10$^6$ centipoise and 55% cylomethicone); General Electric Company
[3]Diamino-functional silicone, m.w. 76,000; SWS Silicone, inc.
[4]Total cyclomethicone, including that contained in the silicone premix described in note 2.
[5]Mixture of 87% Isobutane and 13% propane (by weight of total propellant)

What is claimed is:

1. Anhydrous antiperspirant compositions comprising:
   (a) from about 0.1% to about 30% by weight of an antiperspirant active;
   (b) from about 0.01% to about 20% by weight of a solid, water-soluble, skin active agent other than the antiperspirant or deodorant active;
   (c) from about 0.1% to about 40% by weight of a suspending agent; and
   (d) from about 10% to about 99% by weight of an anhydrous carrier liquid;
   wherein the compositions are substantially free of nonvolatile organic liquids having a C log P value greater than about 7.0.

2. An anhydrous composition according to claim 1, wherein the solid, water-soluble skin active agent comprises a solid, water-soluble vitamin.

3. An anhydrous composition according to claim 2, wherein the composition contains less than 3% by weight of free or added water.

4. An anhydrous composition according to claim 2, wherein the solid, water-soluble vitamin comprises Vitamin B.

5. An anhydrous composition according to claim 2, wherein the water-soluble vitamin is selected from the group consisting niacinamide, nicotinic acid, nicotinyl alcohol, nicotinic acid esters of $C_1$–$C_{22}$ alcohols, tocopherol nicotinate, inositol hexanicotinate, nicotinyl amino acids, 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl)urea, 2-mercaptonicotinic acid, nicomol, niaprazine, thiamine, riboflavin, pantothenic acid, pyridoxine, cyanocobalamine, ascorbic acid, nonvitamin skin nutrients, and combinations thereof.

6. An anhydrous composition according to claim 2, wherein the water-soluble skin active agent comprises niacinamide.

7. An anhydrous composition according to claim 2, wherein the composition is in the form of a soft solid or cream.

8. An anhydrous composition according to claim 2, wherein the composition is in the form of a solid stick.

9. An anhydrous composition according to claim 1, wherein the composition is in liquid form.

10. An anhydrous composition according to claim 2, wherein the antiperspirant active represents from about 5% to about 30% by weight of the composition, and wherein the antiperspirant active is selected from the group consisting of aluminum-containing active, zirconium-containing active, and combinations thereof.

11. An anhydrous composition according to claim 2, wherein the antiperspirant active is selected from the group consisting aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

12. An anhydrous composition according to claim 11, wherein the antiperspirant active is in the form of solid particulates.

13. An anhydrous composition according to claim 2, wherein the anhydrous carrier comprises a volatile silicone at concentrations ranging from about 5% to about 70%, by weight of the composition.

14. An anhydrous composition according to claim 2, wherein the anhydrous carrier comprises a non-volatile silicone liquid that represents from about 1% to about 35% by weight of the composition.

15. An anhydrous composition according to claim 2, wherein the composition is in the form of a solid stick having a Residue Grade of less than about 40.

16. An anhydrous composition according to claim 1, wherein the solid, water-soluble skin active agent is selected from the group consisting of vitamins, topical pharmaceuticals, hair growth inhibitors, non-vitamin nutrients, and combinations thereof.

17. An anhydrous composition according to claim 2, wherein the composition contains less than 1% by weight of the high C log P solvents.

18. An anhydrous composition according to claim 2, wherein the composition contains zero percent by weight of the high C log P solvents.

19. An anhydrous composition according to claim 2, wherein compositions are substantially free of nonvolatile organic liquids having a C log P value greater than about 7.2.

20. An anhydrous composition according to claim 2, wherein the suspending agent comprises a silicone elastomer at concentrations ranging from about 0.1% to about 10%, by weight of the composition.

21. An anhydrous composition according to claim 2, wherein the suspending agent is a solid material selected from the group consisting of hydrogenated castor oil, fatty alcohol, silicone wax, silicone elastomer, and combinations thereof.

22. An anhydrous composition according to claim 2, wherein the antiperspirant active is in the form of solid particulates having an having an average particle diameter of from about 1 $\mu$m to about 40 $\mu$m and wherein the average particle diameter of the antiperspirant active and the solid skin active agent differs by not more than about 40 $\mu$m.

23. An anhydrous composition according to claim 22, wherein the solid skin active agent has an average particle size of from about 1 $\mu$m to about 40 $\mu$m.

24. Anhydrous deodorant compositions comprising:
(a) from about 0.1% to about 30% by weight of an antimicrobial deodorant active;
(b) from about 0.1% to about 20% by weight of a solid, water-soluble, skin active agent other than the deodorant active;
(c) from about 0.1% to about 40% by weight of a suspending agent; and
(d) from about 10% to about 99% by weight of an anhydrous carrier liquid;
wherein the compositions are substantially free of nonvolatile organic liquids having a C log P value greater than about 7.0.

25. An anhydrous composition according to claim 24, wherein the solid, water-soluble skin active agent comprises a solid, water-soluble vitamin.

26. An anhydrous composition according to claim 25, wherein the solid, water-soluble vitamin comprises Vitamin B.

27. An anhydrous composition according to claim 25, wherein the deodorant active represents from about 0.1% to about 5% by weight of the composition and is selected from the group consisting of triclocarban, triclosan, and combinations thereof.

28. An anhydrous composition according to claim 25, wherein the composition contains zero percent by weight of the high C log P solvents.

29. An anhydrous composition according to claim 25, wherein compositions are substantially free of nonvolatile organic liquids having a C log P value greater than about 7.2.

30. An anhydrous composition according to claim 25, wherein the suspending agent comprises a fatty acid salt.

31. An anhydrous composition according to claim 30, wherein the suspending agent comprises sodium stearate.

32. An anhydrous composition according to claim 25, wherein the water-soluble skin active agent is selected from the group consisting niacinamide, nicotinic acid, nicotinyl alcohol, nicotinic acid esters of $C_1$–$C_{22}$ alcohols, tocopherol nicotinate, inositol hexanicotinate, nicotinyl amino acids, 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl)urea, 2-mercaptonicotinic acid, nicomol, niaprazine, thiamine, riboflavin, pantothenic acid, pyridoxine, cyanocobalamine, ascorbic acid, nonvitamin skin nutrients, and combinations thereof.

33. An anhydrous composition according to claim 25, wherein the water-soluble skin active agent comprises niacinamide.

34. A method of reducing underarm perspiration wetness and odor, said method comprising the application of from about 0.1 gm to about 20 gram per underarm of the anhydrous antiperspirant composition of claim 2.

35. The method of claim 34, wherein the composition is applied to a shaven underarm.

36. A method of reducing underarm odor, said method comprising the application of from about 0.1 gm to about 20 gram per underarm of the anhydrous deodorant composition of claim 25.

37. A method of making anhydrous antiperspirant and deodorant compositions, said method comprising the steps of
(a) preparing an intermediate composition by mixing together the following components:
  (i) from about 0.1% to about 30% by weight of a solid, antiperspirant or deodorant active;
  (ii) from about 0.01% to about 20% by weight of a solid, water-soluble, skin active agent other than the antiperspirant or deodorant active;
  (iii) from about 0.1% to about 40% by weight of a suspending agent; and
  (iv) from about 10% to about 99% by weight of an anhydrous carrier liquid that is substantially free of nonvolatile organic liquids having a C log P value greater than about 7.0;
(b) heating the intermediate composition to above the melting point of the suspending agent to form a liquid intermediate composition containing solid antiperspirant active and solid, water-soluble, skin active agent, and solid aggregates thereof;
(c) milling the liquid intermediate composition for a period of time sufficient to reduce the average particle diameter of the solid aggregates to less than 50 µm; and then
(d) pouring the milled liquid intermediate into a dispensing package and allowing the packaged composition to cool to ambient temperatures, to form an anhydrous antiperspirant and deodorant composition.

38. The method of claim 37, wherein the skin active agent comprises a solid, water-soluble vitamin and the anhydrous antiperspirant and deodorant composition contains less than 3% by weight of free or added water.

39. The method of claim 38, wherein the water-soluble vitamin comprises niacinamide.

40. The method of claim 38 wherein the antiperspirant or deodorant active is selected from the group consisting of aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentatchlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, aluminum chloride, aluminum sulfate buffered, and combinations thereof.

* * * * *